United States Patent [19]
Sullivan et al.

[11] Patent Number: 5,713,925
[45] Date of Patent: Feb. 3, 1998

[54] ADAPTER FOR ISOLATING PACING AND DEFIBRILLATION SIGNALS

[75] Inventors: Joseph L. Sullivan, Kirkland; Bret R. Warrick, Graham; James M. Pihl, Woodinville, all of Wash.

[73] Assignee: Physio-Control Corporation, Redmond, Wash.

[21] Appl. No.: 585,159

[22] Filed: Jan. 11, 1996

[51] Int. Cl.⁶ .................. A61N 1/36; A61N 1/39; A61N 1/362

[52] U.S. Cl. .................. 607/4; 607/142; 607/148; 607/5

[58] Field of Search .................. 607/4, 5, 115, 607/142, 148, 2

[56] References Cited

U.S. PATENT DOCUMENTS

| | | | |
|---|---|---|---|
| 3,547,108 | 12/1970 | Seiffert | 607/5 |
| 4,097,113 | 6/1978 | McKelvy | 607/5 |
| 4,419,998 | 12/1983 | Heath | 607/142 |
| 4,494,552 | 1/1985 | Heath | 128/696 |
| 4,628,935 | 12/1986 | Jones et al. | 607/4 |
| 4,635,639 | 1/1987 | Hakala et al. | 607/4 |
| 4,827,936 | 5/1989 | Pless et al. | 607/4 |
| 4,915,109 | 4/1990 | Daynes et al. | 607/2 |
| 4,955,381 | 9/1990 | Way et al. | 607/4 |
| 5,044,367 | 9/1991 | Endres et al. | 607/4 |
| 5,080,097 | 1/1992 | Eisenberg | 607/4 |
| 5,080,099 | 1/1992 | Way et al. | 607/4 |
| 5,148,805 | 9/1992 | Schamberg | 607/2 |
| 5,184,620 | 2/1993 | Cudahy et al. | 607/4 |
| 5,284,135 | 2/1994 | Lopin | 607/4 |
| 5,334,045 | 8/1994 | Cappa et al. | 439/506 |
| 5,443,490 | 8/1995 | Flugstad | 607/5 |
| 5,540,722 | 7/1996 | Clare et al. | 607/5 |

*Primary Examiner*—William E. Kamm
*Assistant Examiner*—Carl H. Layno
*Attorney, Agent, or Firm*—Christensen, O'Connor, Johnson & Kindness PLLC

[57] ABSTRACT

An adapter for connecting combination electrodes to a defibrillator/monitor/pacer. The adapter isolates the pacer from the defibrillator when a defibrillation pulse is applied over the combination electrodes. In a first embodiment of the adapter, the pacer is conductively connected to the combination electrodes only when the pacer's power supply is turned on. In a second embodiment of the adapter, the pacer is normally connected to the combination electrodes, but is disconnected when the defibrillator/monitor/pacer is analyzing a patient's ECG or when the defibrillator is charging to enable it to deliver a defibrillation pulse. Also provided in the adapter is a contact assembly for connecting the adapter to defibrillation paddles from the defibrillator.

27 Claims, 10 Drawing Sheets

ADAPTER FOR ISOLATING PACING AND DEFIBRILLATION SIGNALS

FIELD OF THE INVENTION

This invention relates to physiological instruments, and more specifically to an adapter that connects to a defibrillator/monitor/pacer to isolate pacing and defibrillation signals.

BACKGROUND OF THE INVENTION

Today's emergency medical technician (EMT) increasingly relies upon a sophisticated array of instruments when responding to medical emergencies. For example, most well equipped EMTs now carry portable defibrillator/monitor/pacers for responding to emergencies involving persons with heart problems. A defibrillator/monitor/pacer is a physiological instrument which provides the capability of defibrillation, pacing, or monitoring of a person's heart by use of a single instrument. As those skilled in the art will recognize, defibrillation involves the application of a high-energy pulse to a heart that has begun to fibrillate in order to return the heart to a normal rate. Pacing involves the regular application of a low-energy pulse to keep the heart beating at a steady rate. And monitoring involves detecting and displaying the electrical signals generated by a beating heart, more typically known as an electrocardiogram (ECG). Portable units which incorporate all three of these functions are manufactured by the assignee of the current application, Physio-Control Corp., and include devices sold under the trademarks LIFEPAK 9P and LIFEPAK 10.

The first defibrillator/monitor/pacers used separate electrodes to apply cardiac stimulation signals to the patient. Pacing was performed with a set of electrodes that were temporarily attached to a patient using an adhesive. Defibrillation was typically performed with a dedicated set of defibrillation paddles. When defibrillation of a person's heart was required, the paddles were charged and applied to both sides of the patient's chest.

Using separate paddles and pacing electrodes was found to be very unwieldy for several reasons. First, the use of paddles to apply defibrillation pulses placed an EMT in dangerously close proximity to the location where energy was being delivered to a patient. Since defibrillation pulses are of extremely high energy, EMTs holding onto the paddles were placed at risk of electrical shock if they contacted the paddles or accidentally touched the patient while holding the paddles in place. Second, it was impossible to optimally place the paddles on a patient. Testing has shown that defibrillation has the greatest chance of success when the high voltage pulse is applied between a patient's chest and back. Ideally, one of the paddles should therefore be located on the front of the patient, and the other on the back. When using conventional hand-held paddles, it was nearly impossible for an EMT to safely locate the paddles in this manner. Finally, using separate electrodes for pacing and defibrillation added complexity to an already difficult situation. EMTs normally treat their patients at accident scenes or other less-than-optimal locations. The addition of extra electrodes and the difficulty in placement of the defibrillation paddles made an EMT's job all the more difficult.

To overcome the disadvantages of using separate defibrillation and pacing electrodes, several manufacturers developed combination electrodes which allow for pacing and defibrillation to take place over the same set of electrodes. When using combination electrodes, a first electrode is placed on the chest of the patient, and a second electrode is placed on the side of the patient. The electrodes are designed so that monitoring may be continuously performed in order to detect abnormalities in the beating of the heart. When emergency conditions are detected, a defibrillation or pacing pulse may be applied through the combination electrodes. The use of combination electrodes therefore simplifies the application of pacing and defibrillation pulses. It also increases the safety for the EMT, who can remotely trigger when a defibrillation pulse is to be applied to a patient experiencing heart fibrillation.

While the use of combination electrodes has been a great help to EMTs, incorporating combination electrodes into existing portable defibrillator/monitor/pacers has proved to be a challenging problem. When using combination electrodes, pacing and defibrillation signals are provided over the same electrode pad. The pacer and defibrillator must therefore be electrically isolated so that the energy of a defibrillation pulse generated by the defibrillator is not shunted by the pacer. This problem is especially acute because to be effective on a patient, the defibrillation pulses must have a high amplitude. Unless the defibrillation pulses are somehow isolated from the pacer, the pacer circuitry would typically absorb the majority of the energy of a defibrillation pulse that is meant to be delivered to a patient. It is also advantageous to isolate the pacer circuitry from the defibrillator to prevent damage to the pacer from the high amplitude defibrillation pulses.

Several different approaches have been taken to separate a pacer from other physiological instruments producing cardiac stimulation signals. For example, a simple switch may be used to alternate between defibrillation and pacing signals. If a device has an internal defibrillator and pacer, a user-controlled mechanical switch may be provided to select whether the defibrillator signal or the pacing signal is output on a set of conducting electrodes.

A slightly different approach is shown in U.S. Pat. No. 4,955,381 to Way et al. Way describes the use of a "pass-through," which contains an asynchronous external cardiac pacemaker. The pass-through is connected to a defibrillator by two spring-loaded plates located on its upper surface. The plates are sized to allow defibrillator paddles to be pressed down on the plates, and spring-loaded so that they are normally protruding above the upper surface of the pass-through. When the spring-loaded plates are protruding, the pass-through allows pacer signals to be fed directly to electrodes that are attached to a patient. When the defibrillation paddles are pressed against the plates, however, the springs compress and complete an electrical connection between the paddles and the electrodes connected to the patient. In this position, the electrical connection with the pacer is disconnected and defibrillation pulses may be applied to the patient. The movement of the spring-loaded plates therefore prevents shunting of energy by the pacer by disconnecting the pacer circuitry when a defibrillation pulse is applied.

Still another method of separating a pacer and a defibrillator is suggested by U.S. Pat. No. 4,419,998 to Heath. Heath suggests placing a high-voltage protection circuit between the defibrillator and the pacer and/or between the defibrillator and a monitor. The high-voltage protection includes a network of resistors, capacitors, and diodes to reduce the amplitude of high-voltage pulses generated by the defibrillator. The protection circuit is a passive network which automatically limits the defibrillation voltage to a level that will not damage the pacer or monitor circuitry and also reduces the energy that is shunted by the pacer circuitry.

While the three methods discussed above prevent defibrillation pulses from being shunted by the pacer circuitry, each method can only be practiced in certain environments. That is, often times it is impossible to retroactively apply these techniques to existing combination defibrillator/monitor/pacers. For example, not all defibrillator/monitor/pacers have signal-isolating switches for conveniently selecting between defibrillation and pacing signals. Similarly, it is not always feasible to retroactively add spring-loaded platforms that are shaped to receive defibrillator paddles, or specialized protection circuitry. It would therefore be advantageous to develop alternative methods of isolating pacer circuitry from defibrillation circuitry in those environments where the techniques discussed above may not be applied.

SUMMARY OF THE INVENTION

The present invention provides an adapter for isolating pacer circuitry from defibrillation circuitry when applying pacing and defibrillation signals over combination electrodes. In one embodiment of this invention, the defibrillator and pacer outputs are connected by an adapter that contains a relay controlled by the pacer power supply. When the pacer power supply is activated, the relay is actuated (closed) to connect the pacer with the external outputs that lead to the combination electrodes. When a defibrillation pulse is to be applied, the pacer power supply is automatically turned off, which automatically opens the relay between the pacer and the defibrillator. This ensures that the high-voltage pulse that is delivered to the combination electrodes by the defibrillator is not conducted to the pacer circuitry. Because the pacer power supply is only activated when pacing therapy is applied, and not when defibrillation is applied, the pacer and the defibrillator will never be simultaneously coupled to the combination electrodes when defibrillator pulses are applied.

In a second embodiment of the invention, the defibrillator and the pacer are similarly isolated using an adapter containing a relay. Instead of controlling the relay with the pacer power supply, however, two signals that are inherent in many defibrillator/monitor/pacers are used. When a defibrillator pulse is to be applied to a patient, the defibrillator must charge to a specified energy level. When the charge is complete, most defibrillators have some form of audible or visual warning indicating that the paddles have been fully charged and are ready for use. One signal that may be used to control the isolation of the pacer from the defibrillator is therefore the signal indicating that electrodes are charging or are charged. When the "charge" signal indicates that the paddles are charging or have been charged, the relay between the pacer and the defibrillator is opened, isolating the pacer so that the defibrillation pulse may be applied to the patient without being shunted by the pacer circuitry.

Many defibrillators also contain a supplemental system to automatically analyze when or if it is necessary to apply a defibrillation pulse to a patient. Such a system is manufactured by Physio-Control, the assignee of the current invention, and sold under the trademark Shock Advisory System (SAS). Before beginning defibrillation, defibrillators with this capacity will monitor a patient's heartbeat to determine if it is necessary to apply a defibrillation pulse. During this period, pacing should not be applied to the patient so that accurate readings may be taken of the patient's ECG. Therefore, a second signal that may be used as an indication to isolate the pacer from the defibrillator is a signal indicating when a patient's ECG is being analyzed. When the "analyze" signal indicates that the Shock Advisory System is monitoring the patient's waveform to determine whether to apply a defibrillation pulse, the pacer is isolated from the defibrillator circuit by opening the relay.

It will be recognized that the novel use of signals inherently present in most combination defibrillator/monitor/pacers simplifies the retrofitting of an adapter for isolating the outputs from the defibrillator and pacer for use with combination electrodes. Because the isolation of the pacer from the defibrillator is performed by a relay, the electrical isolation is nearly absolute.

It is also a further feature of this invention to include within an adapter a retractable contact assembly for connecting the adapter to a set of defibrillator paddles. Because an adapter must carry defibrillator energy from the defibrillator to a set of combination electrodes, it is often easier to receive this energy from the set of defibrillator paddles, rather than by directly wiring the adapter into the defibrillator. In the present invention, a contact assembly is therefore provided which makes electrical contact between each paddle and the adapter. A defibrillation pulse generated by the defibrillator is thereby provided to the adapter via contacts contained on the contact assembly.

Connecting the adapter to the defibrillator using the defibrillator paddles provides additional flexibility to the system. There are often circumstances when EMTs would rather use the defibrillator paddles directly. For example, there may be situations where there are problems with using combination electrodes, where the pacing function provided by combination electrodes is clearly not necessary, or where the supply of disposable combination electrodes has been exhausted. In these circumstances, EMTs would like to use the defibrillator paddles directly. In the present invention, the paddles may be removed from the adapter and used directly to apply defibrillation pulses. It is a safety feature of this invention to provide a retracting mechanism for withdrawing the contacts into the adapter when the defibrillator paddles are removed. Withdrawing the contacts ensures that no high-voltage points are exposed on the adapter when using the defibrillator paddles directly.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
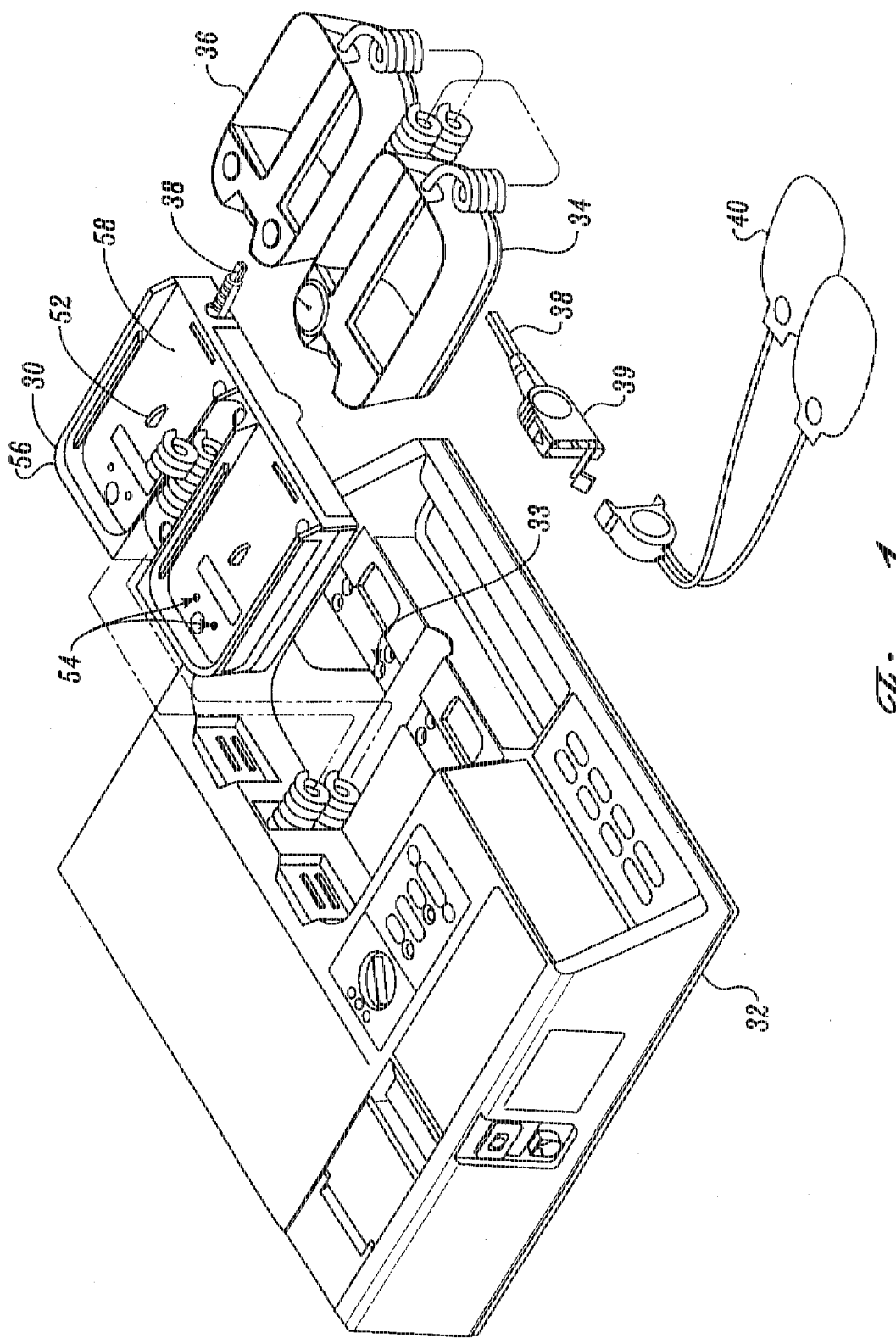
FIG. 1 is a top perspective of an overall system incorporating a first embodiment of an adapter for isolating pacing and defibrillation signals in accordance with the present invention, including a defibrillator/monitor/pacer, defibrillator paddles, and set of combination electrodes.

In accordance with the present invention, FIG. 1 depicts a first embodiment of an adapter 30 that is designed to combine the defibrillator and the pacer outputs from a defibrillator/pacer/monitor 32 for use with combination electrodes. To perform this function, the adapter must isolate the pacer during application of defibrillation pulses. The defibrillator/monitor/pacer shown in FIG. 1 is a LIFEPAK 10, manufactured by Physio-Control Corp., the assignee of the current application. As shown in FIG. 1, adapter 30 is sized to fit within a cradle on a defibrillator/monitor/pacer 32. It will be appreciated that adapter 30 may also be sized to attach to other defibrillators/monitors/pacers other than the LIFEPAK 10.

Once positioned in the cradle of the defibrillator/monitor/pacer 32, adapter 30 is electrically connected to the pacer and the defibrillator. The adapter is electrically connected to the defibrillator via defibrillator paddles 34 and 36. Defibrillator paddles 34 and 36 are conventional paddles in that they have plastic nonconducting handles and conducting electrode plates secured to the bottom surface of the handles. When used, the bottom electrodes are placed against a patient and buttons on the handles are simultaneously depressed to apply a defibrillation pulse. Paddles 34 and 36 slide onto the upper surface of the adapter, where they are secured by mounting flanges. As will be described in further detail, the paddles provide an electrical connection from the defibrillator to the adapter.

The adapter is electrically connected to the pacer by directly wiring the adapter to the pacer. This connection is made through a hole 33 in the bottom of the cradle of the defibrillator/monitor/pacer 32. In the first embodiment of the present invention, the adapter is therefore permanently mounted to the portable system. The connection with the pacer will similarly be described in more detail below.

After being connected to the defibrillator/monitor/pacer, the adapter allows the use of combination electrodes to provide pacing and defibrillation signals to a patient. Attached to adapter 30 is a cable 38 that includes a plug 39 sized to connect to a set of disposable combination electrodes 40. Adapter 30 is designed to conduct both the pacer output and the defibrillator output from defibrillator/monitor/pacer 32 to combination electrodes 40. More importantly, adapter 30 provides isolation between the defibrillator and the pacer so that defibrillation signals will not shunt energy from the defibrillator or damage the pacer circuitry.

Figure 2:
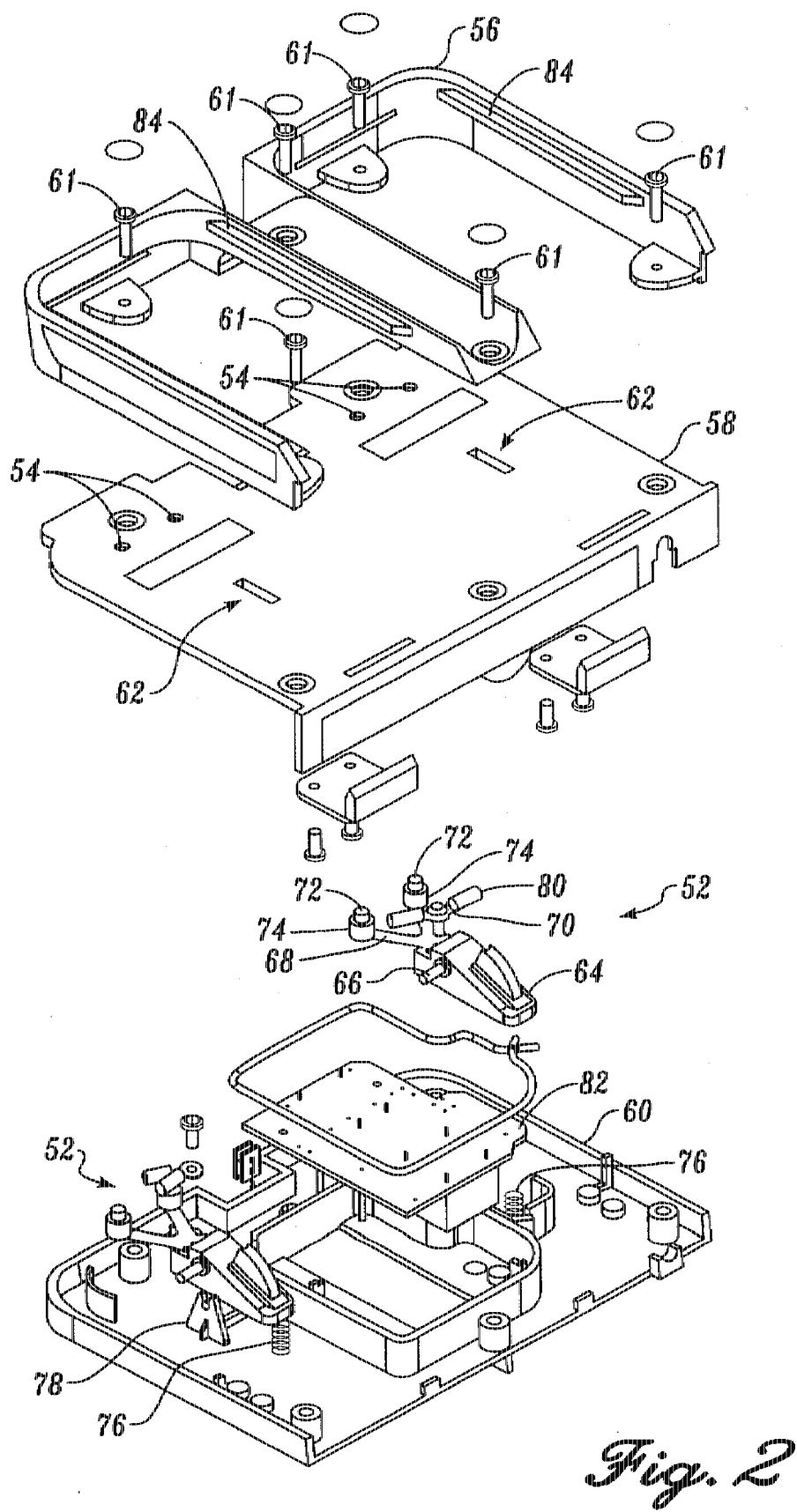
FIG. 2 is a top perspective of the first embodiment of the adapter with parts shown in exploded relationship.

The internal construction of adapter 30 is shown in FIG. 2. The main structural components of adapter 30 are formed of a nonconducting plastic and comprise an upper bracket 56, a central paddle plate 58, and a bottom base 60. These three components are fastened together with a series of screws 61 that clamp the paddle plate between the bracket and the base. Bracket 56 is designed to hold the bottom electrodes of paddles 34 and 36 (FIG. 1) against paddle plate 58. To accomplish this, bracket 56 includes a series of horizontal flanges 84 that are positioned at an appropriate height so that the defibrillation paddles may be slid snugly beneath the flanges into the bracket and maintained in position by friction with the paddle electrodes engaged against plate 58. To make electrical contact between the defibrillation paddle electrodes and the electrical circuitry of the adapter, two contact assemblies 52 are provided in each adapter. Contact assemblies 52 have conductive contact points 72 that project through holes 54 in the adapter plate 58 when the defibrillation paddles are located in bracket 56 of the adapter. When the defibrillation paddles have been removed from bracket 56, however, the electrical connection between contact points 72 and the defibrillation paddle electrodes is broken, and the contact points are automatically withdrawn so that a user of the adapter cannot come into contact with any exposed electrical parts.

As shown in FIG. 2, each contact assembly 52 is seated in a mount 78 that is integrally formed in base 60 of the adapter. There are two contact assemblies, one disposed under each paddle. Each contact assembly 52 includes a molded body 64 having a separate metal shaft 66 that extends through the molded body and protrudes from both sides. Metal shaft 66 is cradled in the associated mount 78 so that body 64 pivots about a horizontal axis spaced below central paddle plate 58. Attached to body 64 is a V-shaped conductor 68 extending generally horizontally and transversely of the axis of metal shaft 66. The arms of conductor 68 terminate at enlarged travel stops 74 and upward projecting contact points 72. Conductor 68 is attached to body 64 by a screw 70. A compression spring 76 is positioned under the body of the contact assembly at the opposite side of mount 78 from conductor 68 to bias the contact assembly to a withdrawn position with conductor 68 swung down. That is, the spring acts to push the contact assembly body into contact with the bottom of paddle plate 58. Paddle plate 58 has two apertures 62 that are sized to allow an upward projecting tab 65 of contact assembly body 64 to protrude above the top of the paddle plate. When the paddles are not positioned in adapter 30, spring 76 ensures that the contact assembly body 64 will be pushed against the paddle plate so that tab 65 is protruding through aperture 62. The withdrawn position is maintained until the paddles are inserted into the adapter.

Figure 3:
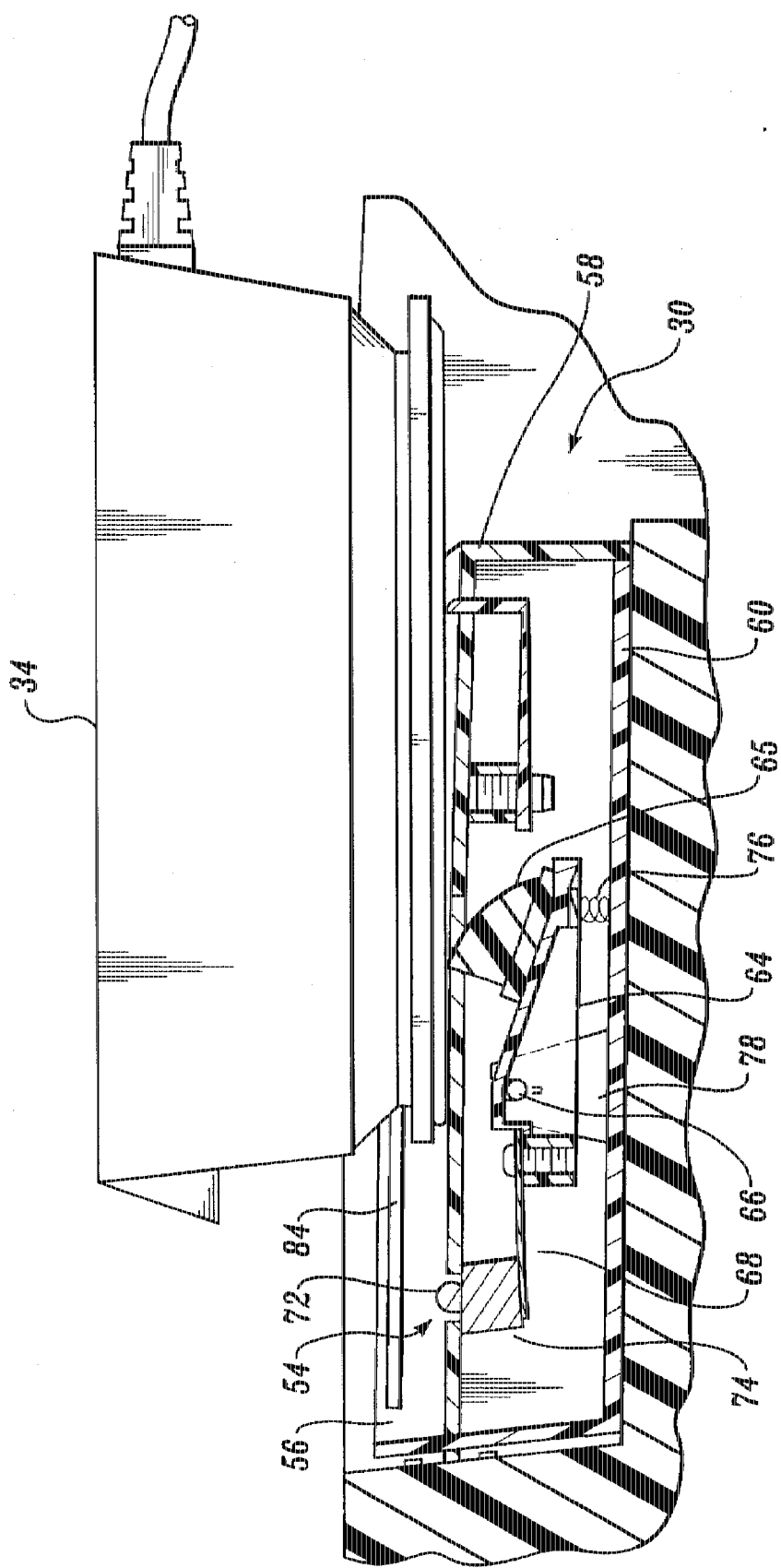
FIG. 3 is an enlarged side elevation of the first embodiment of the adapter, with parts broken away, showing the position of a defibrillator contact assembly with defibrillation paddles inserted partially into the adapter.
Figure 4:
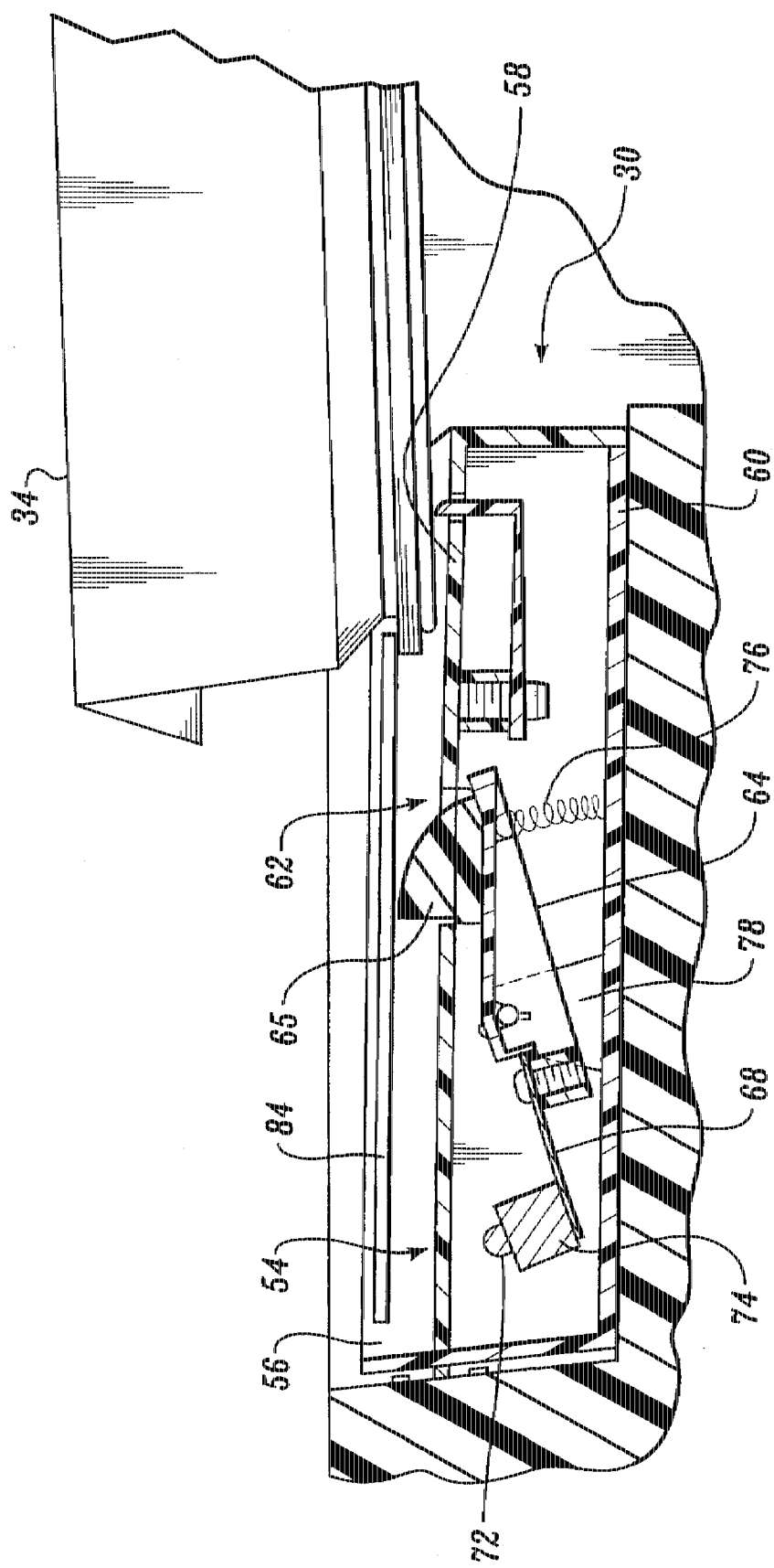
FIG. 4 is an enlarged side elevation corresponding to FIG. 3, but with parts in different positions, namely, with the paddles largely removed from the adapter.

The operation of contact assembly 52 is best shown in the cross-sectional views of FIGS. 3 and 4. FIG. 3 shows the position of the contact assembly with a paddle partially engaged in bracket 56. When a paddle, such as paddle 34, is slid into bracket 56 of adapter 30, the bottom electrode of the paddle initially forces tab 65 of the associated contact assembly 52 beneath the top of paddle plate 58 against the biasing force of spring 76. Conductor 68 is simultaneously raised due to the pivotal mounting of the contact body 64 in mount 78. As conductor 68 is raised, contact points 72 move up through holes 54, causing the contact points to protrude above the top of paddle plate 58. The distance the contact points protrude above the surface of the paddle plate is limited by travel stops 74, which are larger than holes 54. The travel stops are biased against the paddle plate due to the action of V-shaped conductor 68, which is a flexible member that acts as a spring. The flexibility of the conductor ensures that the travel stop will always bear against paddle plate 58. The flexibility of the conductor also ensures that contact points 72 will fully protrude though holes 54 in paddle plate 58 regardless of any slight mislocation of the contact assembly body relative to paddle plate 58. In a preferred embodiment of the invention, conductor 68 is constructed of spring steel, a material which exhibits the desired flexibility.

The further insertion of paddle 34 in bracket 56 brings the bottom electrode of the paddle into contact with contact points 72. As the paddle slides under the bracket flange, the paddle electrode slides over contact points 72. The sliding motion rubs off any contamination on the contact points, resulting in a low resistance electrical connection between the paddle electrodes and the contact points. The complete insertion of the paddle causes conductor 68 to slightly flex as the electrode comes into contact with the contact points. The flexing of the conductor ensures that contact points 72 will always bear against the paddle electrode, with the stiffness of the conductor determining the force that is exerted by the contact points. The use of two contact points 72 per paddle electrode ensures that a redundant electrical circuit is provided in case one contact point becomes contaminated. If one contact point were to fail, the other contact point is capable of carrying the entire defibrillation pulse energy. In a preferred embodiment of the invention, contact points 72 are made of silver cadmium oxide to carry the large defibrillation current. With both paddles inserted into the adapter bracket, defibrillation pulses applied over the paddles are conducted through the paddle electrodes, contact points 72, and into the adapter. The defibrillation pulses can then be applied to a patient over a set of combination electrodes connected to the adapter.

As seen in FIG. 4, when the paddles are removed from adapter 30, each spring 76 exerts an upward force on the contact assembly body 64 to return the conductor 68 including contact points 72 to the withdraw position. As the opposite end of the body is raised, contact points 72 are lowered below the top of paddle plate 58. In the fully retracted position, contact points 72 and conductor 68 are located entirely beneath paddle plate 58. Because the contact points are no longer exposed, it is nearly impossible for a person near the adapter to come into contact with any dangerous electrical potential.

Allowing independent access to the defibrillation paddles is advantageous in that it allows the paddles to be used as a backup in case the combination electrodes fail. That is, if a malfunction were to occur when using combination electrodes, an EMT could remove the defibrillation paddles and use them to apply defibrillation pulses to a patient. When the defibrillation paddles are removed, the safety of the adapter is maintained by withdrawing the contact points used to make electrical contact with the defibrillator electrodes.

Returning to FIG. 2, adapter 30 contains internal wiring to receive the pacing and defibrillation signals from the defibrillator/monitor/pacer and to connect the signals to the attached combination electrodes. A circuit board 82 mounted in adapter base 60 contains all of the electrical components for isolating the pacer from the defibrillator when defibrillation pulses are applied to a patient. Circuit board 82 is connected to contact assembly 52 by wires (not shown) leading to connectors 80 which, in turn, are connected to conductors 68. These allow defibrillation pulses to be received from the defibrillation paddles by way of the contact points. Circuit board 82 is also directly wired (not shown) to the pacer in defibrillator/monitor/pacer 32. The defibrillation and pacer signals are then combined for output to a set of combination electrodes. A block diagram of these electrical connections is provided in FIG. 5.

Figure 5:
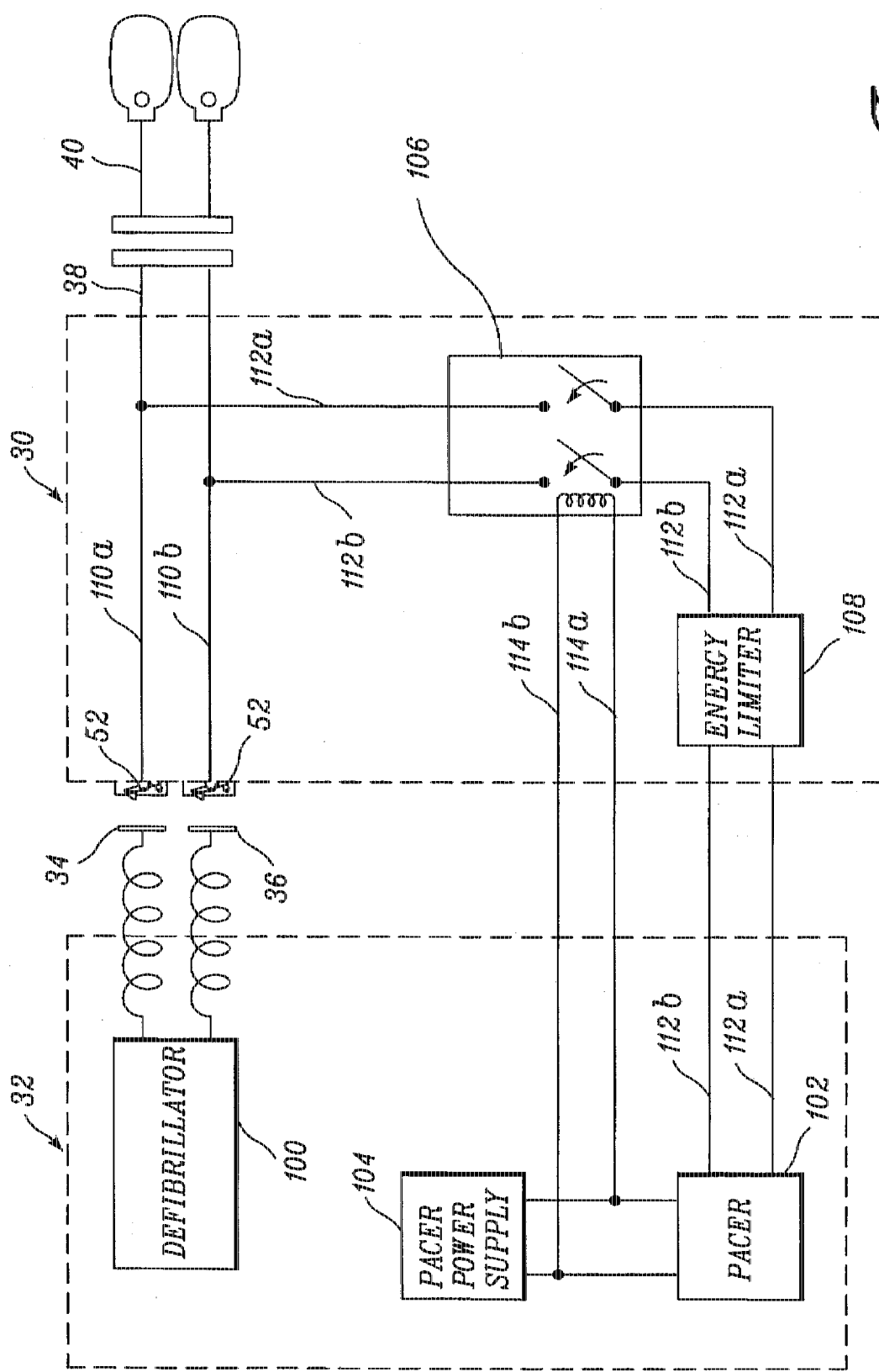
FIG. 5 is a block diagram of the electrical circuitry of the first embodiment of the adapter.

A combination defibrillator/monitor/pacer 32 and adapter 30 are shown in block diagram form in FIG. 5. The components of defibrillator/monitor/pacer 32 include a defibrillator pulse generator 100, pacer circuitry 102, and a pacer power supply 104. Pacer power supply 104 is used to provide power to the pacer circuitry when a pacing signal is to be delivered to a patient. Defibrillator pulse generator 100 is connected to paddles 34 and 36 for application of defibrillation pulses to a patient. As was shown in FIG. 1, adapter 30 is designed to electrically mate with combination defibrillator/monitor/pacer 32 at several points. First, defibrillator pulse generator 100 is coupled to adapter 30 through the defibrillator paddles and contact assemblies 52. As was shown with reference to FIGS. 3 and 4, contact assemblies 52 are brought into contact with paddles 34 and 36 when the paddles are slid into adapter 30. Second, pacer 102 is directly wired to adapter 30. Those skilled in the art will recognize that although the preferred embodiment of the adapter is directly wired to the LIFEPAK 10, the connection to adapter 30 could be made with any cable or removable connector. Finally, in the first embodiment of the adapter, adapter 30 is also directly wired to pacer power supply 104. This allows adapter 30 to receive an indication that the pacer power supply is turned on. Again, those skilled in the art will recognize that a removable connector could be used to make this connection.

Within adapter 30, contact assemblies 52 are directly wired via leads 110a and 110b to combination electrode cable 38. This allows defibrillation pulses to be directly applied from defibrillator pulse generator 100 to combination electrodes 40. Connected to leads 110a and 110b are leads 112a and 112b from pacer circuitry 102. As shown in FIG. 5, these leads first pass through an energy limiter 108 and a relay 106. Relay 106 is normally open, meaning that the pacer leads 112a and 112b are normally not electrically connected to the defibrillator leads 110a and 110b.

In operation, adapter 30 will always conduct defibrillation pulses from defibrillator pulse generator 100 to combination electrodes 40 due to the direct connection of leads 110a and 110b, so long as the paddles 34 and 36 are inserted into the adapter. This allows an EMT at any time to apply a defibrillation pulse to a patient experiencing heart failure. When pacing is to be applied to a patient, however, the EMT selects the pacing option on the combination defibrillator/monitor/pacer 32. Selecting pacing therapy turns on pacer power supply 104, and enables pacer circuitry 102. When the pacer power supply is turned on, the voltage generated by the power supply is applied to relay 106, thereby closing the relay and connecting pacer circuitry 102 with leads 110a and 110b. This allows pacing signals to be applied from pacer circuitry 102 to combination electrodes 40. Relay 106 stays closed as long as pacing pulses are applied, i.e., until the EMT discontinues the selection of the pacing mode of operation.

When an EMT switches from pacing to defibrillation, the defibrillator is selected on the defibrillator/monitor/pacer. This turns pacer power supply 104 off, opens relay 106, and breaks the connection between the pacing leads and the defibrillator leads. Constructing adapter 30 in this manner ensures that the defibrillation pulses will never be applied across the pacer. Whenever defibrillation pulses are to be applied, the pacer power supply will always be off.

Figure 6:
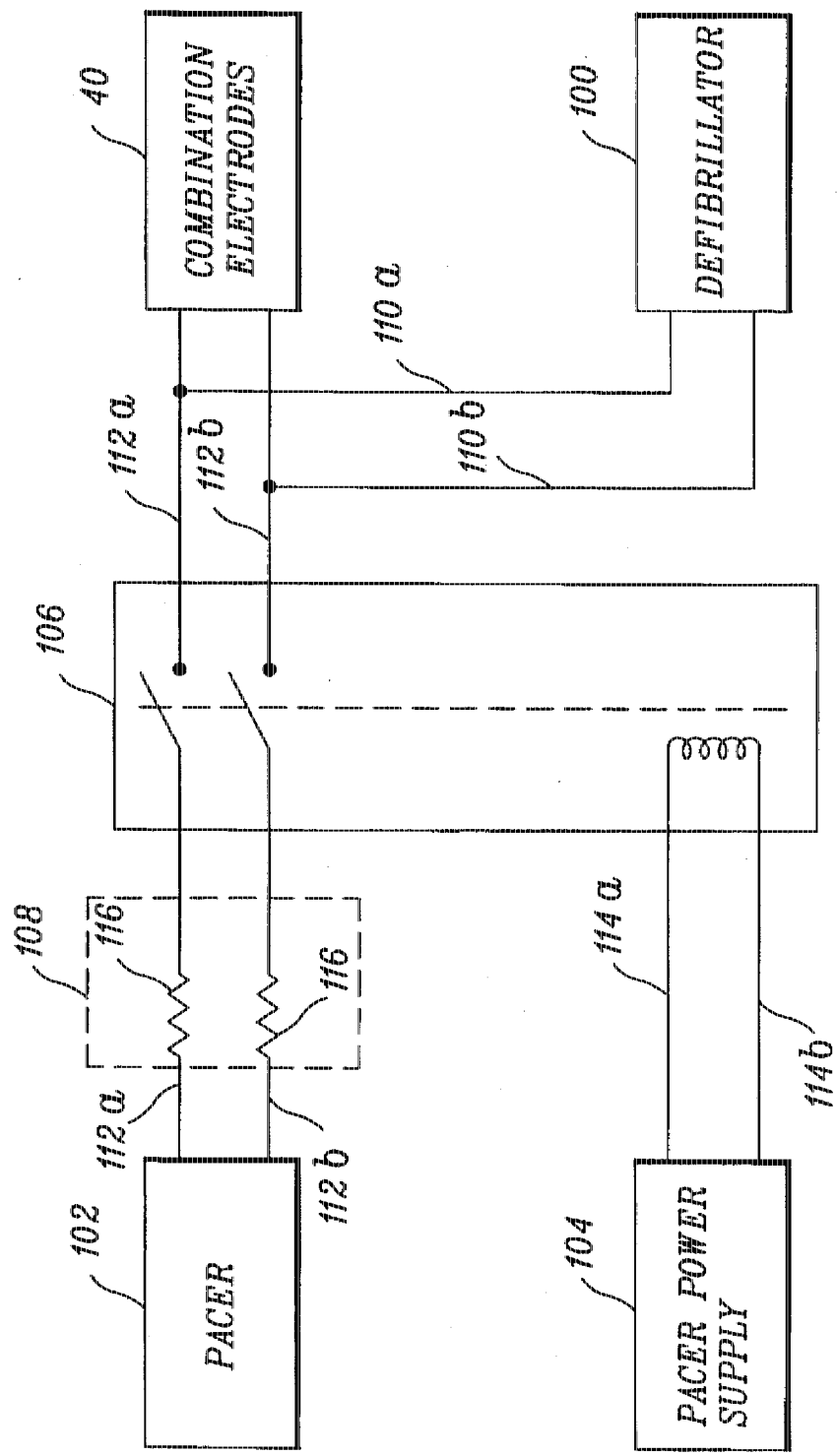
FIG. 6 is a partial schematic of the first embodiment of the adapter.

FIG. 6 is an electrical schematic of the first embodiment of adapter 30. As shown in FIG. 6, defibrillator pulse generator 100 is connected to combination electrodes 40 via leads 110a and 110b. Also coupled to leads 110a and 110b are the outputs from pacer circuitry 102, identified as leads 112a and 112b. The outputs from the pacer circuitry are coupled to the defibrillator leads by normally-open relay 106. Normally-open relay 106 is controlled by the output from pacer power supply 104. When pacer power supply 104 is turned on, the voltage between leads 114a and 114b closes relay 106, allowing the pacing output to be applied to the combination electrodes.

Also coupled to leads 112a and 112b is energy limiter 108. As shown in FIG. 6, energy limiter 108 consists of two resistors 116 in series with the pacer output leads. The energy limiter is present to mitigate damage that may be caused when a third party connects a second defibrillator to a patient which is already connected to a defibrillator/pacer/monitor by a set of combination electrodes. If pacing therapy is being applied to the patient through the combination electrodes when the third party attempts to apply a defibrillation pulse, part of the energy of the defibrillation pulse would be shunted through the combination electrodes, relay 106, and pacer circuitry 102. Energy limiter 108 is therefore present to minimize the amount of energy that would be shunted to pacer circuitry 102 when a third-party defibrillation pulse is applied and to limit the current through the contacts of relay 106. The values for resistors 116 are selected to minimize the amount of current that would be conducted back to the pacer. In a preferred embodiment of the invention, resistors 116 are rated at 300 ohm, 2 watts, to limit the amount of defibrillation energy shunted from the patient to less than 15% of the third-party defibrillation pulse that is applied to the patient when tested with a 100 ohm patient and a 10 ohm series resistance between the two electrode sets.

Figure 7:
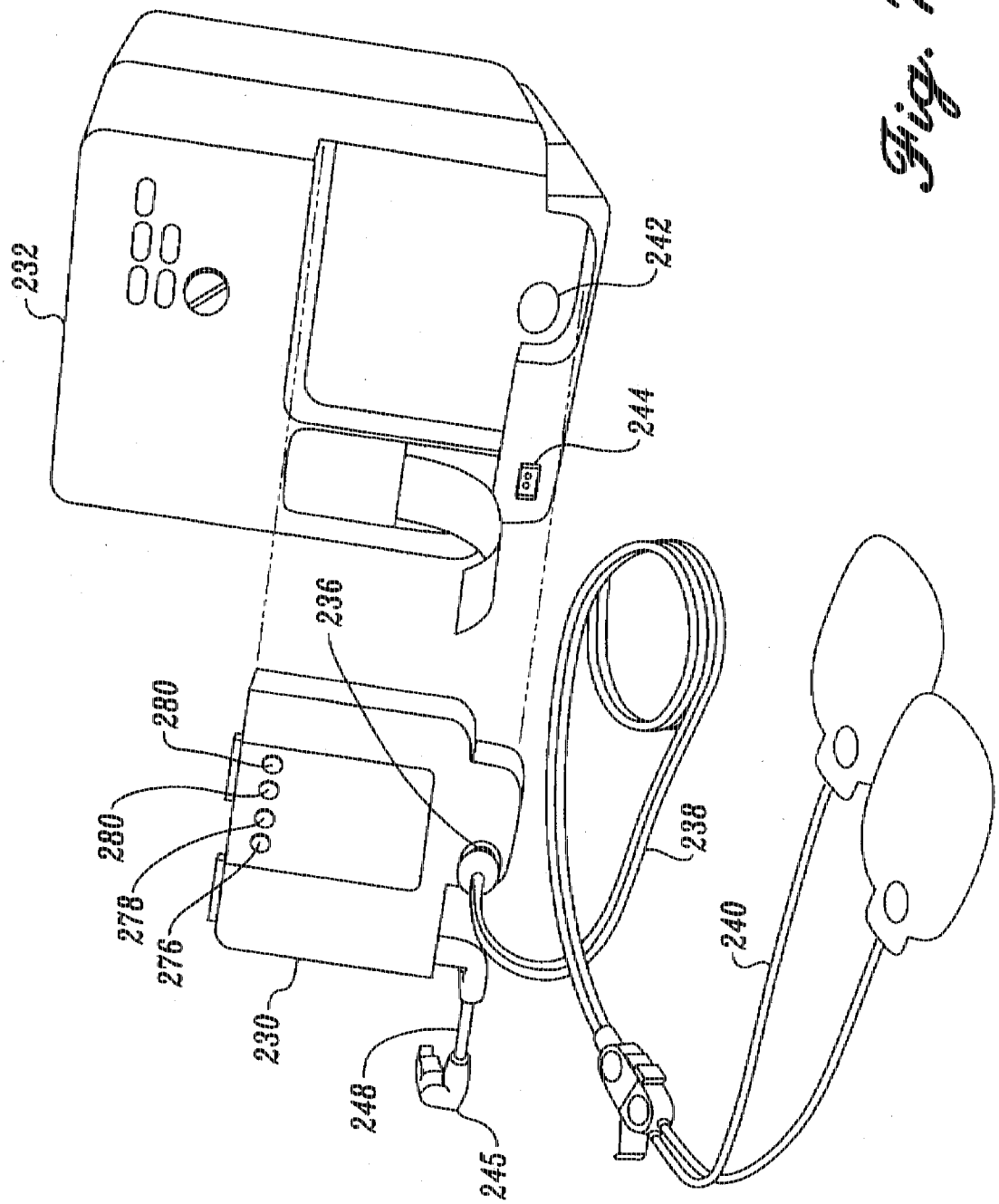
FIG. 7 is a top perspective of a second embodiment of an adapter in accordance with the present invention as used in a portable defibrillator/monitor/pacer.

In the second embodiment of the present invention, shown in FIG. 7, an adapter 230 designed to isolate a pacer from a defibrillator is sized to fit within a cradle on defibrillator/monitor/pacer 232. The defibrillator/monitor/pacer shown in FIG. 7 is a LIFEPAK 9P, manufactured by Physio-Control Corp., the assignee of the current application. It will be appreciated that adapter 230 may also be sized to fit cradles contained on other defibrillator/monitor/pacers other than the LIFEPAK 9P.

Unlike the first embodiment of the adapter, in which adapter 30 is hard-wired into the defibrillator/monitor/pacer, adapter 230 may be easily inserted and removed from the physiological instrument. The removal of the adapter is facilitated by connectors present on the LIFEPAK 9P, which allow the adapter to be quickly and easily connected to both the defibrillator and pacer outputs. Adapter 230 specifically has two electrical connection points with the LIFEPAK 9P. As shown in FIG. 7, a connector 242 is present which provides power and status signals to adapter 230 and also links adapter 230 with the defibrillator output of the defibrillator/monitor/pacer. Adapter 230 is configured with a complimentary connector 246 to mate with connector 242. A connector 244 is also present on the LIFEPAK 9P to provide the pacer output to adapter 230. Adapter 230 contains a cable 248 having a connector 245 to connect the adapter with the pacer output at connector 244.

Once positioned in the cradle of defibrillator/monitor/pacer 232, adapter 230 may be connected to a set of combination electrodes 240. A connector 236 is provided on adapter 230 that may be connected to an electrode cable 238. Electrode cable 238 incorporates a plug that may be linked with combination electrodes 240. Adapter 230 allows both pacing and defibrillation signals to be conducted over cable 238 to combination electrodes 240. More importantly, as did the first embodiment of the adapter, adapter 230 also provides isolation between the defibrillator and the pacer so that defibrillation signals will not shunt defibrillator energy or damage the pacer circuitry.

Figure 8:
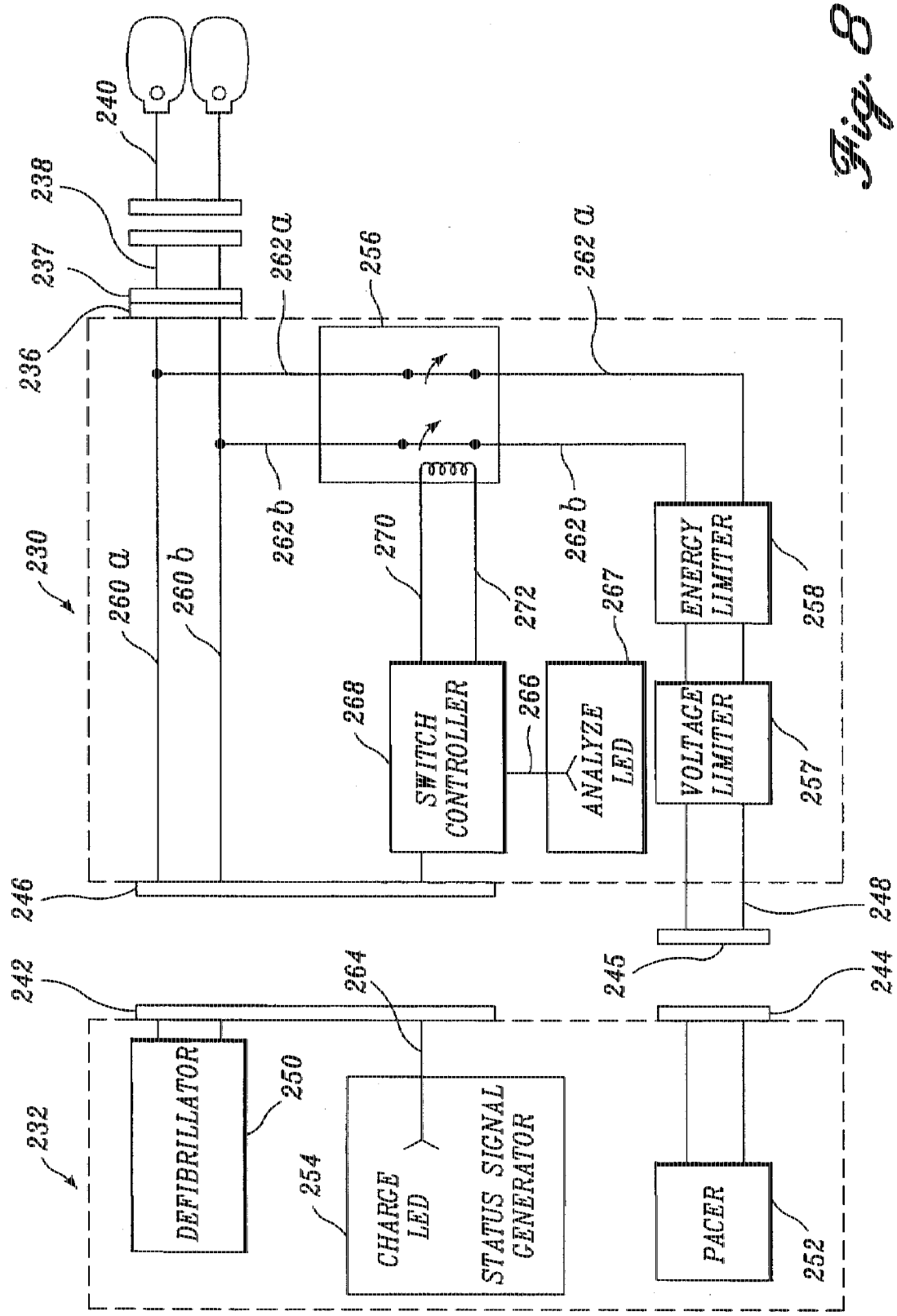
FIG. 8 is a block diagram of the electrical circuitry of the second embodiment of the adapter.

The internal circuitry of adapter 230 and defibrillator/monitor/pacer 232 are shown in block diagram form in FIG. 8. Defibrillator/monitor/pacer 232 is composed of a defibrillator pulse generator 250, pacer circuitry 252, and a status signal generator 254 that provides a "charge" signal on a line 264. Adapter 230 connects to the defibrillator pulse generator and status signal generator outputs of the defibrillator/monitor/pacer 232 by mating connector 242 with connector 246. An extension cable 248 is also provided to connect the adapter with the pacer output by mating connector 244 with connector 245. In the LIFEPAK 9P, the pacer output is provided at a location remote from where the adapter is seated.

Within adapter 230, leads 260a and 260b, which carry the defibrillator pulse, are directly wired from connector 246 to connector 236. This allows defibrillation pulses to be directly conducted from defibrillator pulse generator 250 to combination electrodes 240 through a connector 237 and cable 238. Coupled to leads 260a and 260b are leads 262a and 262b, which carry the pacing signal from pacer circuitry 252. As shown in FIG. 8, these leads first pass through a voltage limiter 257, an energy limiter 258, and a normally-closed relay 256. Relay 256 is normally closed, meaning that pacer leads 262a and 262b are normally connected to defibrillator leads 260a and 260b. Also connected to relay 256 via lines 270 and 272 is a switch controller 268. Switch controller 268 receives a signal from the status signal generator of the defibrillator/monitor/pacer indicating that the system is charging on line 264, and a signal indicating that the system is analyzing an ECG on a line 266 from a status signal generator 267 located within the adapter.

During adapter operation, relay 256 is normally closed, allowing pacing signals from pacer circuitry 252 to be conducted through adapter 230 and cable 238 to combination electrodes 240. In this configuration, a clinician may apply pacing therapy to a patient experiencing an irregular heartbeat. Alternatively, a patient may be experiencing heart problems which require defibrillation therapy. To make this determination, many defibrillators/monitors/pacers are equipped with a means for analyzing a patient's ECG and automatically determining whether defibrillation is required. An adapter that can be used with the LIFEPAK 9P for this purpose is sold under the name Shock Advisory System (SAS) by Physio-Control. For purposes of this description, it will be assumed that adapter 230 includes a Shock Advisory System to analyze ECGs to determine if defibrillation is necessary.

As part of the SAS, adapter 230 contains four buttons. As shown in FIG. 7, the front of the adapter contains an analyze button 276, a charge button 278, and two shock buttons 280. When the ECG of a patient is to be checked for an irregular rhythm, a clinician pushes the analyze button. The SAS proceeds to monitor the patient's heartbeat to determine if it is appropriate to apply a defibrillation pulse to the heart. While this analysis is being performed, combination defibrillator/monitor/pacer 232 normally provides an indication to the clinician that the analysis is taking place. In the LIFEPAK 9P, the defibrillator/monitor/pacer 232 indicates that analysis is being performed by illuminating an LED (not shown) located near button 276. Adapter 230 uses the signal illuminating the "analyze" LED to control relay 256 shown in FIG. 8. That is, when the analyze LED is lit, switch controller 268 receives a signal on line 266 and opens normally-closed relay 256. This disconnects pacer circuitry 252 from leads 260a and 260b, which will carry the defibrillation pulse. Although it technically is not necessary to separate the defibrillator from the pacer during the analyze period, isolating the defibrillator ensures that the pacing pulse generator will not interfere with the sensitive ECG analysis.

If the result of the SAS analysis indicates that defibrillation should be applied to a patient, a clinician will press charge button 278 to charge the defibrillator. In an actual embodiment of adapter 230, the defibrillator pulse generator indicates that it is charging by flashing an LED (not shown) located near button 278. When defibrillator pulse generator 250 has charged to a point where it is ready to deliver a defibrillation pulse, status signal generator 254 steadily lights the LED. The charge LED remains lit until the defibrillator is discharged through a patient or times out after a preset period. Adapter 230 also uses this "charge" signal to control relay 256. When the charge LED is initially lit, switch controller 268 receives the signal on line 264 and opens normally-closed relay 256. Opening the switch isolates pacer circuitry 252 from defibrillator pulse generator 250 until the charge from the defibrillator paddles has been discharged into a patient. In this manner, adapter 230 maintains an isolation between pacer circuitry 252 and defibrillator pulse generator 250 whenever defibrillation pulses are being applied. It will be recognized by those skilled in the art that the same general isolation technique is applied in the first and second embodiments of the adapter, but different control signals are used to control the operation of the isolation relay.

Figure 9:
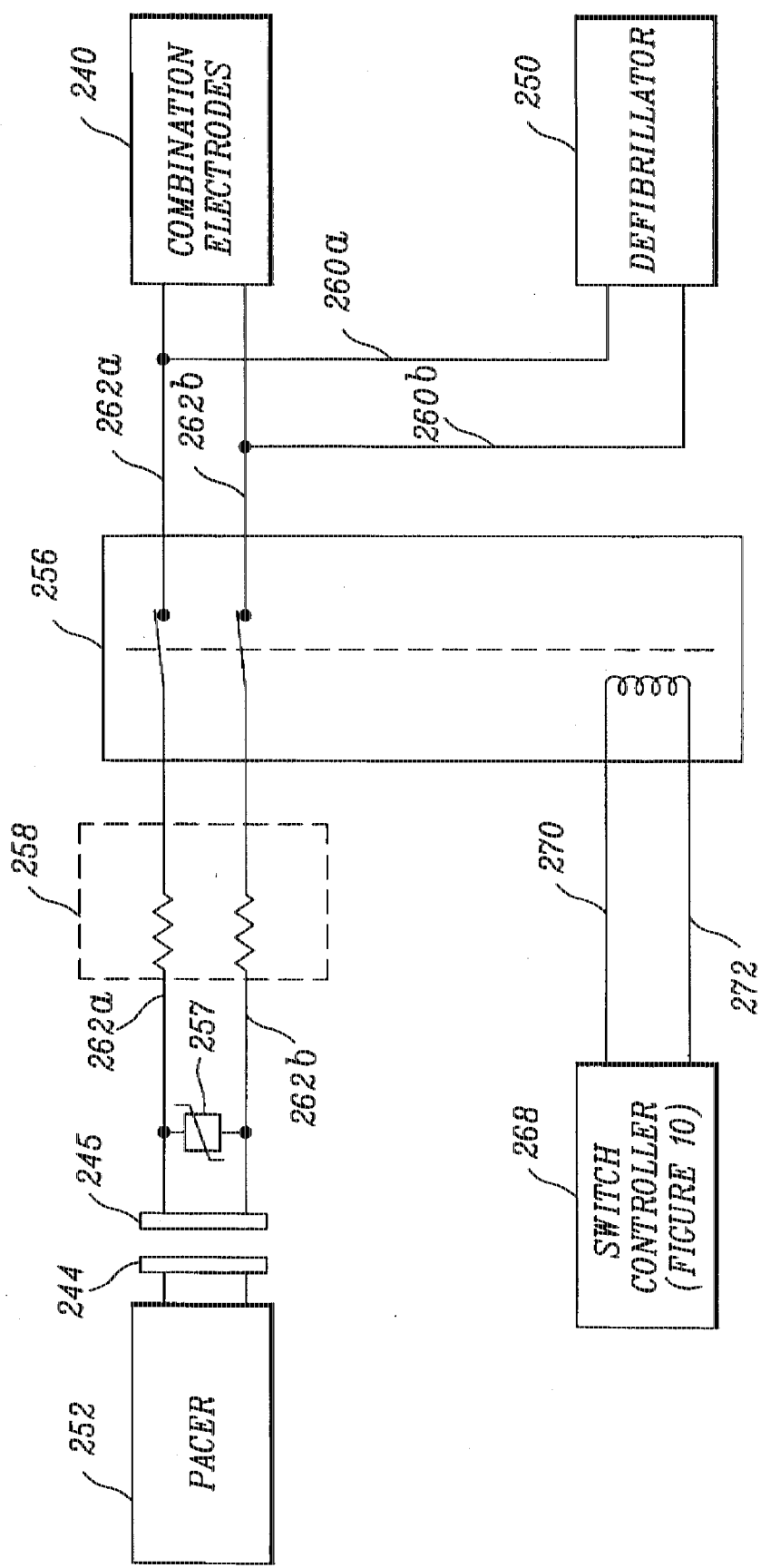
FIG. 9 is a partial schematic of the second embodiment of the adapter, including a switch controller.

FIG. 9 is a electric schematic of the second embodiment of adapter 230. As shown in FIG. 9, defibrillator pulse generator 250 is connected to combination electrodes 240 via leads 260a and 260b. Also coupled to leads 260a and 260b are the outputs from pacer circuitry 252, identified as leads 262a and 262b. The outputs from the pacer circuitry are coupled to the defibrillator leads by normally-closed relay 256. Normally-closed relay 256 is controlled by switch controller 268, whose construction will be discussed with respect to FIG. 10.

Also coupled to leads 262a and 262b is voltage limiter 257 and energy limiter 258. As shown in FIG. 9, energy limiter 258 consists of two resistors in series with the pacer output leads 262a and 262b. As was discussed with respect to the first embodiment of the adapter, the purpose of the energy limiter is to minimize the energy shunted from a patient if a defibrillation pulse is applied by a third-party defibrillator/monitor/pacer connected to the same patient. Further protection is also provided by voltage limiter 257 contained in the second embodiment of the adapter. Voltage limiter 257 consists of a metal oxide varistor placed across leads 262a and 262b, preferably having a rating of 390 volts. The purpose of the varistor is to clamp the maximum voltage that may appear across the end of cable 248 to a few hundred volts. Again, this is to provide additional safety when a third-party defibrillator is used to apply a defibrillation pulse on the same patient that the adapter is connected to with combination electrodes. If connector 245 had somehow become disconnected from defibrillator/pacer/monitor 232, the defibrillation pulse would potentially reach the end of cable 248 since relay 256 is normally closed. The varistor limits this voltage to a high, but generally non-life threatening, voltage.

Figure 10:
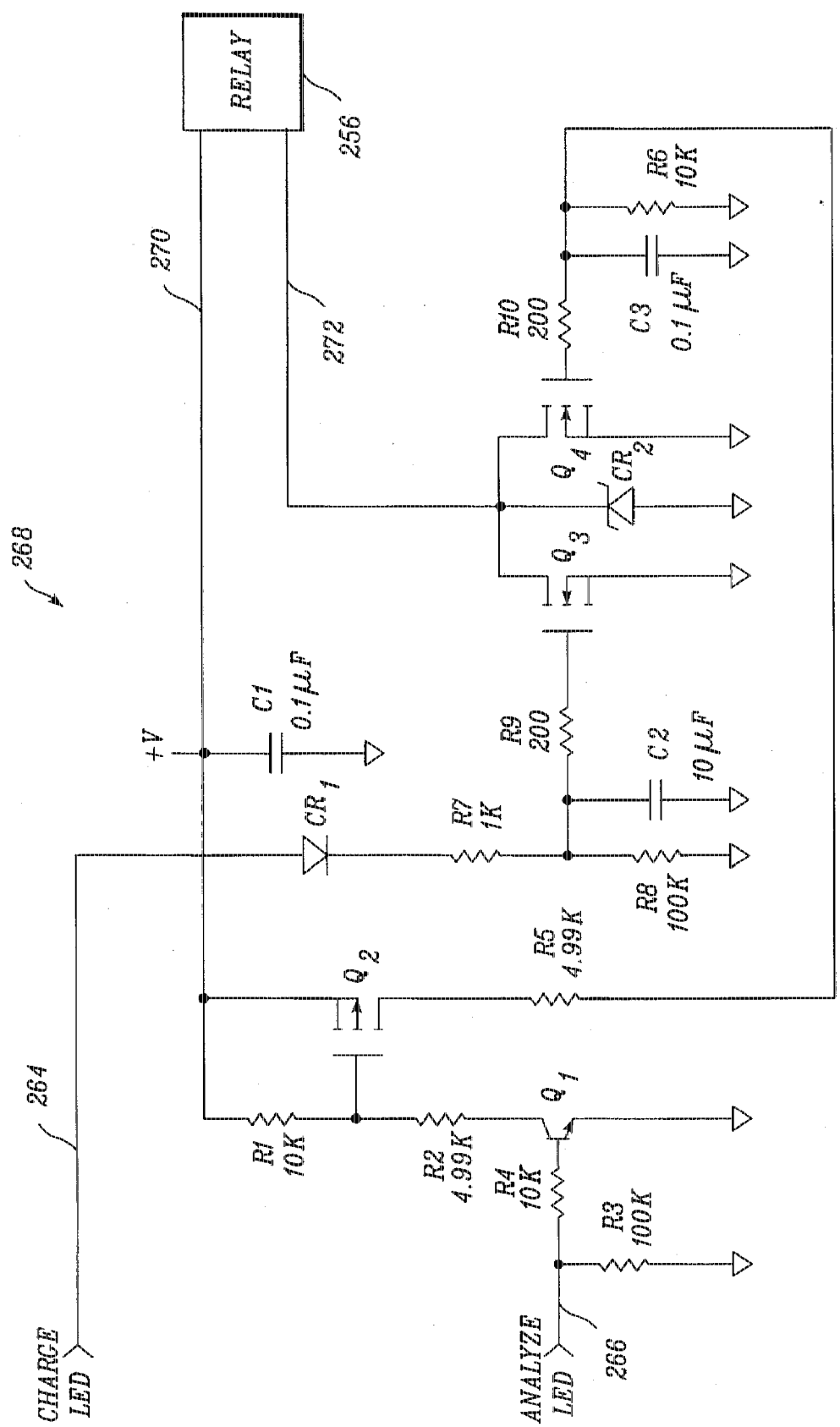
FIG. 10 is a more detailed schematic diagram of one component of the second embodiment of the adapter, namely, the switch controller.

FIG. 10 is a schematic of an actual embodiment of a circuit for use as switch controller 268. The purpose of the circuit is to open relay 256 when either a "charge" or "analyze" signal is received on lines 264 or 266. Because these status signals have different amplitudes and characteristics, however, each signal requires slightly different circuitry to perform this function. In an actual embodiment of the invention, the analyze signal is taken from a low-voltage signal on line 266 that is used to drive the analyze LED. In FIG. 10, the low-voltage signal is used to turn on transistor Q1, which subsequently biases on transistors Q2 and Q4. When Q4 is biased on, current flows from source +V, through the relay on lines 270 and 272, to ground. This opens normally-closed relay 256, isolating the pacing leads from the leads that will carry the defibrillation pulse. When the analyze signal on line 266 is removed, Q4 ceases conducting, allowing normally-closed relay 256 to close.

Similarly, the "charge" signal on line 264 is used to open normally-closed relay 256 when the defibrillator pulse generator is charging. In an actual embodiment of the invention, the charge signal is a 10-12 volt signal that starts with a 50% duty cycle. As was described above, the charge LED flashes to indicate that the defibrillator is charging. After a full charge is reached, the LED remains steady. In order to maintain relay 256 open during the entire charging cycle, the charging signal on line 264 is passed through a network containing a diode CR1 and capacitor C2 before connecting to transistor Q3. The network rectifies and filters the signal to ensure that Q3 will turn on, and remain on, for as long as the charging signal on line 264 is present. When Q3 is turned on, current can flow from source +V through relay 256 to ground. Current flow through the relay opens the normally-closed switch and isolates the pacer circuitry from the defibrillator circuitry. When the defibrillator is discharged, the charge signal on line 264 is removed. Removing the charge signal turns off transistor Q3 and allows normally-closed relay 256 to close. Zener diode CR2 protects transistors Q3 and Q4 from inductive spikes generated by the coil of relay 256.

While the preferred embodiment of the invention has been illustrated and described, it will be appreciated that various changes can be made therein without departing from the spirit and scope of the invention. For example, normally-open relay 106 and normally-closed relay 256 may be any type of switch or circuit that can electrically isolate the pacing leads from the defibrillator leads. Additionally, the electrical connections between the adapter and the defibrillator/monitor/pacer may be made in a number of different ways. In the embodiments discussed above, many of the connections were made with manually disconnectible connectors. Those skilled in the art will recognize that all the connections may instead be made by directly wiring the adapter to the defibrillator/monitor/pacer.

It will also be recognized that other indications that the pacer is activated may be used to control relay 106 other than a voltage obtained across the pacer power supply. For example, some defibrillator/monitor/pacers may use a control signal to enable the pacer power supply when pacing is to be performed. Instead of using the output from the pacer power supply, the enable control signal could be used to close relay 106. Consequently, within the scope of the appended claims it will be appreciated that the invention can be practiced other than as specifically described herein.

The embodiments of the invention in which an exclusive property or privilege is claimed are defined as follows:

1. An adapter for connecting combination electrodes to a physiological instrument having a defibrillator and a pacer including a power supply, the adapter isolating the pacer from the defibrillator when a defibrillation signal is generated by the defibrillator, said adapter comprising:

(a) a pair of defibrillator leads coupleable to the defibrillator for receiving defibrillation signals, said pair of defibrillator leads further being coupleable to the combination electrodes;

(b) a pair of pacing leads coupleable to the pacer for receiving pacing signals;

(c) a control line coupleable to the pacer power supply for receiving a signal indicating whether the power supply of the pacer is on or off, and (d) isolation means coupled to the pair of pacing leads, the pair of defibrillator leads, and the control line, said isolation means electrically isolating the pair of pacing leads from the pair of defibrillation leads in response to the signal on the control line, such that the pair of pacing leads is electrically coupled to the pair of defibrillator leads when the pacing power supply is on, and the pair of pacing leads is not electrically coupled to the pair of defibrillator leads when the pacing power supply is off.

2. The adapter of claim 1, further comprising energy limiting means coupled to the pair of pacing leads for limiting the flow of energy through the pacing leads.

3. The adapter of claim 2, wherein the energy limiting means includes a resistor connected in series with each of said pair of pacing leads.

4. The adapter of claim 1, wherein the isolation means comprises a normally-open relay.

5. The adapter of claim 4, wherein the relay is connected to the power supply of the pacer, such that when the pacer power supply is on, the relay is closed, and when the pacer power supply is off, the relay is open.

6. The adapter of claim 1, in which the physiological instrument includes a pair of defibrillator paddles, further comprising a bracket shaped to receive the pair of defibrillation paddles, said bracket maintaining the pair of defibrillation paddles in electrical connection with the pair of defibrillator leads contained in the adapter.

7. An adapter for connecting combination electrodes to a physiological instrument having a pacer for supplying pacing signals, a defibrillator having a first state in which the defibrillator is charging and a second state in which the defibrillator is charged to supply defibrillation signals, and a status signal generator for generating a status signal indicative of a function being performed by the physiological instrument, the adapter isolating the pacer from the defibrillator when a defibrillation signal is generated by the defibrillator, said adapter comprising:

(a) a pair of defibrillator leads coupleable to the defibrillator for receiving defibrillation signals, said pair of defibrillator leads further being coupleable to the combination electrodes;

(b) a pair of pacing leads coupleable to the pacer for receiving pacing signals;

(c) a control line for receiving a status signal indicative of a function being performed by the physiological instrument; and (d) isolation means coupled to the pair of pacing leads, the pair of defibrillator leads, and the control line, said isolation means electrically isolating the pair of pacing leads from the pair of defibrillation leads in response to the status signal on the control line, such that the pair of pacing leads is not electrically coupled to the pair of defibrillator leads when the status signal is present, and the pair of pacing leads is electrically coupled to the pair of defibrillator leads when the status signal is not present.

8. The adapter of claim 7, further comprising energy limiting means coupled to the pair of pacing leads for limiting the flow of energy through the pacing leads.

9. The adapter of claim 8, wherein the energy limiting means includes a resistor connected in series with each of said pair of pacing leads.

10. The adapter of claim 7, further comprising voltage limiting means coupled to the pair of pacing leads for limiting the voltage potential across the pacing leads.

11. The adapter of claim 10, wherein the voltage limiting means comprises a varistor connected across the pair of pacing leads.

12. The adapter of claim 7, wherein the isolation means comprises a normally-closed relay.

13. The adapter of claim 7, wherein the status signal is a signal indicating that the defibrillator is charging.

14. The adapter of claim 13, wherein the status signal further indicates that the defibrillator is charged.

15. The adapter of claim 7, further comprising means to analyze a patient's ECG to determine if defibrillation should be applied to the patient.

16. The adapter of claim 15, wherein the status signal is a signal indicating that an analysis of a patient's ECG is being performed.

17. An adapter for connecting combination electrodes to a physiological instrument having a pacer, a defibrillator, and a set of defibrillation paddles having bottom electrodes, the adapter isolating the pacer from the defibrillator when a defibrillation signal is generated by the defibrillator, said adapter comprising:

(a) a bracket sized to receive the set of defibrillator paddles;

(b) a nonconducting paddle plate disposed beneath the bracket, said paddle plate having apertures located beneath each of the set of defibrillator paddles;

(c) a pair of contact assemblies disposed beneath said paddle plate and having conducting portions for protruding through the paddle plate apertures, each of said conducting portions being in contact with the bottom electrode of the corresponding defibrillator paddle in order to receive defibrillation pulses from such defibrillator paddle;

(d) a pair of defibrillator leads coupled to the pair of contact assemblies and coupleable to the combination electrodes;

(e) a pair of pacing leads coupleable to the pacer for receiving pacing signals, said pair of pacing leads further being coupleable to the pair of defibrillator leads; and (f) isolation means coupled to the pair of pacing leads and the pair of defibrillator leads, said isolation means electrically isolating the pair of pacing leads from the pair of defibrillation leads when a defibrillation pulse is generated by the defibrillator such that the pair of pacing leads is not electrically coupled to the pair of defibrillator leads when the defibrillation pulse is present, and the pair of pacing leads is electrically coupled to the pair of defibrillator leads when the defibrillation pulse is not present.

18. The adapter of claim 17, wherein the adapter includes a base below the paddle plate, the pair of contact assemblies being pivotally mounted in the base such that the contact assemblies protrude through the paddle plate apertures when the set of defibrillator paddles are disposed in the bracket, and the contact assemblies are withdrawn from the paddle plate apertures when the set of defibrillator paddles is removed from the bracket.

19. The adapter of claim 18, wherein each of the contact assemblies comprises:

(a) a body having a conductive end and a non-conductive end;

(b) cradle means for supporting the body so that it may pivot about a fulcrum located between the ends of the body, said cradle positioned so that when the conductive end of the body is raised the conductive end protrudes through the paddle plate aperture;

(c) biasing means disposed at one end of the body, said biasing means applying a force to the body so that the conductive end of the body is normally withdrawn from the paddle plate aperture; and (d) a tab disposed on the non-conductive end of the body, said tab protruding through a hole in the paddle plate so that when a defibrillator paddle is placed in the bracket the tab is pushed beneath the paddle plate as the tab comes in contact with the bottom of the defibrillator paddle, the tab forcing the body downward and raising the conductive end of the body so that the conductive end of the body will protrude through the paddle plate aperture and come in conductive contact with the electrode on the bottom of the defibrillator paddle.

20. The adapter of claim 19, wherein each of the contact assemblies further comprises a means for holding the biasing means beneath the non-conductive end of the contact assembly body.

21. The adapter of claim 20, wherein the biasing means comprises a spring.

22. The adapter of claim 19, wherein the conductive end of the body comprises a resilient material.

23. The adapter of claim 19, wherein the conductive end of the body further comprises two contact points, each of said contact points protruding through an aperture on the paddle plate.

24. The adapter of claim 23, wherein the conductive end of the body comprises a V-shaped member.

25. An adapter for connecting combination electrodes to a physiological instrument having a pacer for supplying pacing signals, a defibrillator for supplying defibrillation signals, a status signal generator for generating a status signal indicative of a function being performed by the physiological instrument, and an external indicator means for receiving the status signal and for providing an external indication of the state of the status signal, said adapter comprising:

(a) a pair of defibrillator leads coupled to the defibrillator for receiving defibrillation signals;

(b) a pair of pacing leads coupled to the pacer for receiving pacing signals;

(c) a control line for receiving the status signal; and (d) isolation means coupled to the pair of defibrillator leads, the pair of pacing leads and the combination electrodes, said isolation means being switchable between a first coupling state in which the pacing leads are coupled to the combination electrodes and a second coupling state in which the defibrillation leads are coupled to the combination electrodes and the pacing leads are decoupled from the combination electrodes, the state of the isolation means determined by the status signal on the control line.

26. The adapter of claim 25, wherein the eternal indication means comprises a light-emitting diode (LED).

27. The adapter of claim 25, further comprising a bracket shaped to receive a pair of defibrillation paddles, said bracket maintaining the pair of defibrillation paddles in electrical connection with the pair of defibrillator leads contained in the adapter.

* * * * *

UNITED STATES PATENT AND TRADEMARK OFFICE
CERTIFICATE OF CORRECTION

PATENT NO. : 5,713,925
DATED : February 3, 1998
INVENTOR(S) : J.L. Sullivan et al.

It is certified that error appears in the above-identified patent and that said Letters Patent is hereby corrected as shown below:

| COLUMN | LINE | |
|---|---|---|
| 12 (Claim 1, | 67 line 14) | After "off" delete "," and insert therefor --;-- |
| 16 (Claim 26, | 22 line 1) | "eternal" should read --external-- |

Signed and Sealed this

Twenty-eighth Day of April, 1998

Attest:

BRUCE LEHMAN

Attesting Officer

Commissioner of Patents and Trademarks